United States Patent [19]

Citrin

[11] 4,022,207

[45] May 10, 1977

[54] ACTUATOR FOR A SYRINGE

[75] Inventor: Paul S. Citrin, Danbury, Conn.

[73] Assignee: Indicon Inc., Brookfield, Conn.

[22] Filed: Mar. 25, 1976

[21] Appl. No.: 670,358

[52] U.S. Cl. .............................. 128/218 C; 128/236
[51] Int. Cl.² .......................................... A61M 5/00
[58] Field of Search ....... 128/218 R, 218 A, 218 C, 128/218 F, 214 F, 215, 234, 236

[56] References Cited

UNITED STATES PATENTS

| 3,279,653 | 10/1966 | Pfleger | 128/218 A X |
| 3,695,266 | 10/1972 | Lussier | 128/218 C X |
| 3,720,211 | 3/1973 | Kyrias | 128/236 X |
| 3,833,030 | 9/1974 | Waldbauer, Jr. et al. | 128/218 C X |

*Primary Examiner*—John D. Yasko

*Attorney, Agent, or Firm*—St. Onge Mayers Steward & Reens

[57] ABSTRACT

An actuator for a syringe is disclosed with which precise liquid quantities can be dispensed in an accurately repeatable manner with single-hand control. The actuator is formed with a main body shaped to support a syringe whose plunger is moved by a plunger actuator. A reciprocating finger actuatable pusher is mounted with the plunger actuator to the main body and a ratchet mechanism operative between the plunger actuator and the pusher provides discrete motions of the plunger actuator. The main components of the syringe actuator are formed of extruded material and shaped in cross section to conveniently fit together. A back motion inhibitor is employed in the form of a fibrous material capable of restraining reverse movement of the plunger actuator while allowing unobstructed operative movement thereof.

13 Claims, 12 Drawing Figures

U.S. Patent  May 10, 1977  Sheet 1 of 3  4,022,207
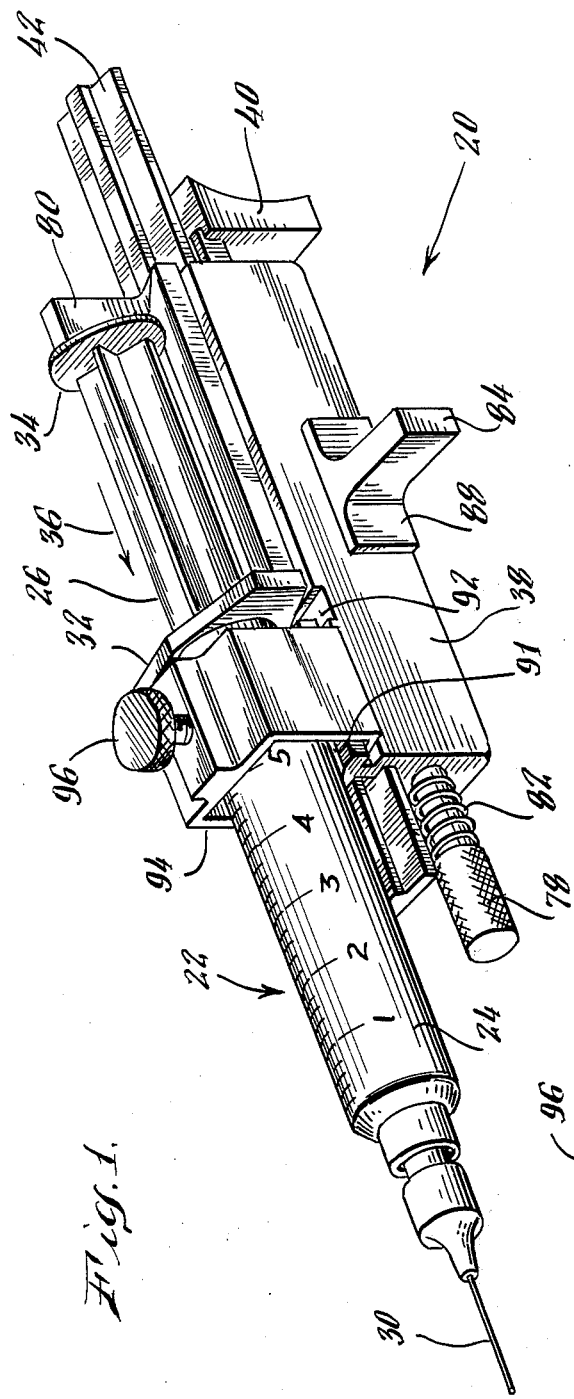
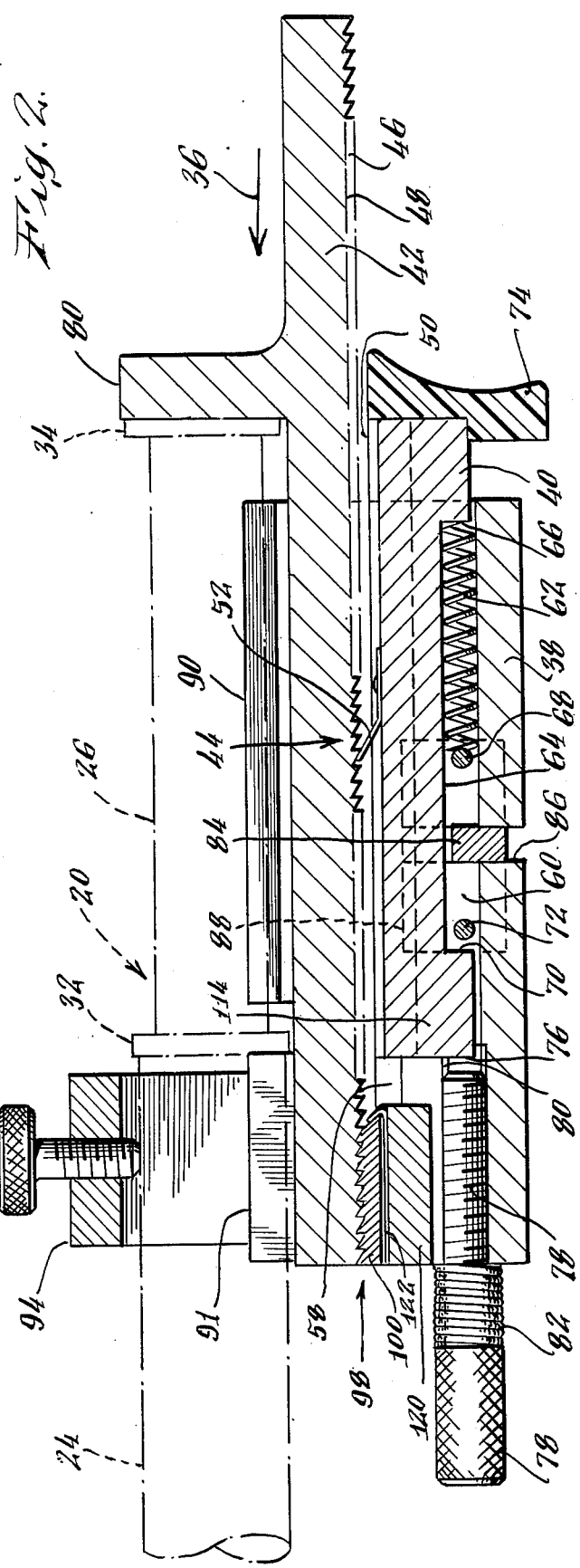

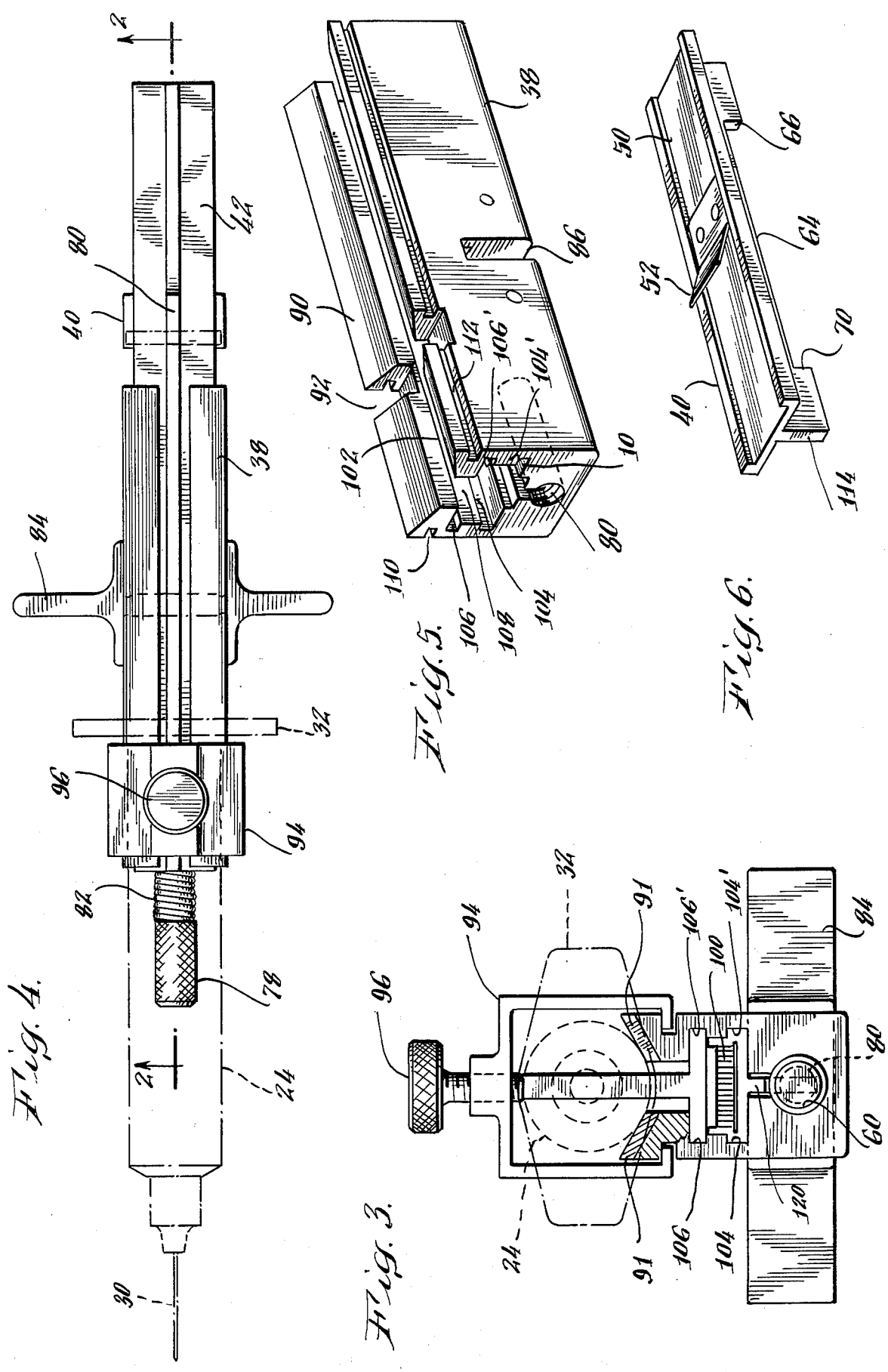

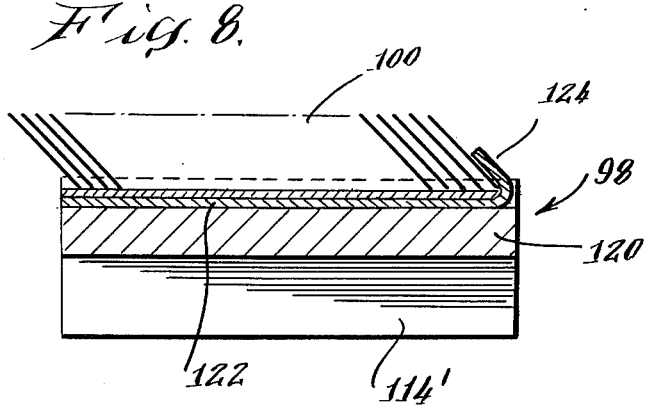
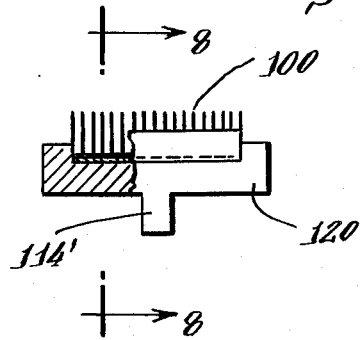
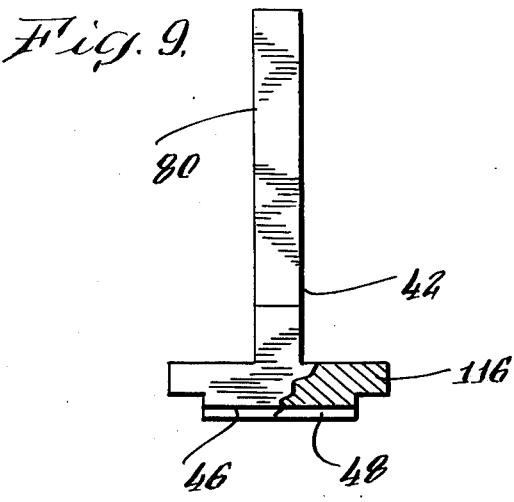
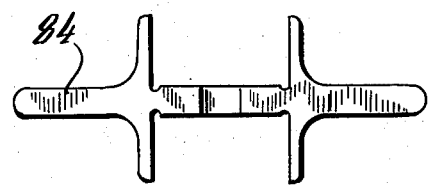
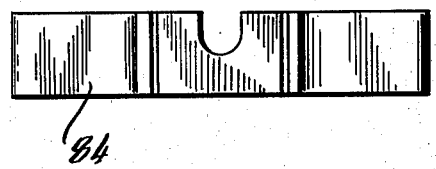
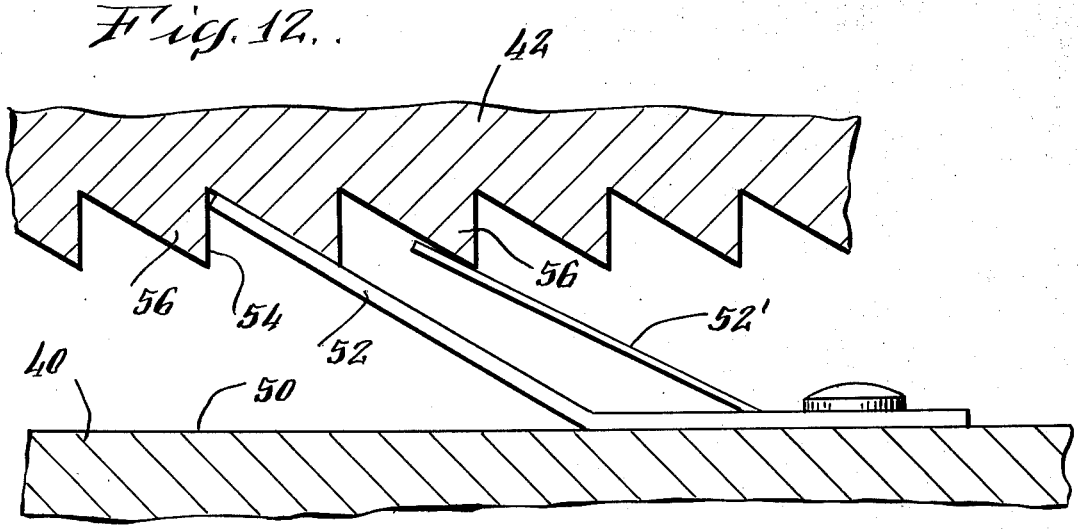

ACTUATOR FOR A SYRINGE

FIELD OF THE INVENTION

This invention relates to a device for actuating a syringe. More specifically, this invention relates to an apparatus for manually actuating a syringe to precisely dispense small quantities of a liquid in a repetetive manner.

BACKGROUND OF THE INVENTION

Syringes are well known in the art and are commonly encountered in fields where small quantities of a liquid are to be disposed. The syringe includes a cylinder for storing the liquid which is dispensed through a narrow nozzle opening by the action of a movable plunger operating in the syringe cylinder. The plunger may be operated either to dispense a liquid or to suck up liquid for storage in the cylinder. The term "liquid transport" as used herein includes both the dispensation or taking up of liquid through the opening of the syringe cylinder.

Syringes come in a great variety of sizes and shapes. Some are made of glass and thus may be reused after cleaning, while others are made of a throw-away material such as plastic.

A need exists to enable a convenient manual transportation of liquid through the opening of a syringe in precise quantities and in a repetetive manner with a device which is convenient to use, economical to produce and of sufficient flexibility to be adapted to a great variety of applications.

SUMMARY OF THE INVENTION

With a syringe actuator in accordance with the invention, precise quantities of a liquid may be transported through the opening of a syringe with a mechanism which advances the syringe plunger in precise repeatable steps. The actuator includes a ratchet mechanism with a back motion inhibitor of a type which enables highly accurate liquid transport, yet with a convenient manual single-hand control.

In accordance with one form for a syringe actuator in accordance with the invention, the majority of the components of the device are formed from extruded metal pieces. A minimum machining work is then needed to complete the components whose assembly onto a syringe actuator is quickly and conveniently completed.

A syringe actuator in accordance with one form of the invention further contemplates a device for varying the stroke of the syringe plunger to obtain a desired quantity of liquid transport. For example, an adjustable stop element may be employed to control the stroke length of the ratchet mechanism. With such stop element, precise multiples of a minimum quantity of liquid may be dispensed with each actuation.

The ratchet mechanism may be conveniently provided with multiple pawls which are so spaced from each other that for any one spacing between rack-teeth used in the ratchet, smaller plunger advance can be obtained. In this manner smaller quantities of liquid can be dispensed with the same rack.

It is, therefore, an object of the invention to provide an actuator for a syringe. It is a further object of the invention to provide a syringe actuator which is convenient to manually actuate to transport liquid in precise small quantities in a repetetive manner.

These and other objects and advantages for a syringe actuator in accordance with the invention can be understood from the following description of a preferred embodiment described in conjunction with the drawings.

BRIEF DESCRIPTION OF DRAWINGS

FIG. 1 is a perspective view of a syringe and actuator in accordance with the invention;

FIG. 2 is a vertically reversed longitudinal section of the syringe actuator taken along the plane defined by line 2—2 in FIG. 4;

FIG. 3 is an end view of the syringe actuator shown in FIG. 1 as taken along the plane defined by line 3-3'

FIG. 4 is a top plan view of the syringe actuator shown in FIG. 1;

FIG. 5 is a perspective view of a main body employed in the syringe actuator of FIG. 1;

FIG. 6 is a perspective view of a finger actuatable pusher used in the syringe actuator of FIG. 1;

FIG. 7 is an end view of a back motion inhibitor employed in the syringe actuator of FIG. 1;

FIG. 8 is a section of the back motion inhibitor taken along the plane defined by line 8—8 in FIG. 7;

FIG. 9 is an end, partial section view of a plunger actuator employed in the syringe actuator of FIG. 1;

FIGS. 10 and 11 are respectively end and top views of a finger tab used with the syringe actuator of FIG. 1; and FIG. 12 is an enlarged section view of a segment of a ratchet mechanism with multiple pawls for use in the syringe actuator of FIG. 1.

DESCRIPTION OF EMBODIMENT

With reference to FIGS. 1 and 2, an actuator 20 in accordance with the invention is shown together with a syringe 22. The syringe, which is of conventional, well known design, may be of the glass type or of a disposable plastic form and includes a cylinder 24 for retaining a liquid and a plunger 26 for causing transport of the liquid through an opening of cylinder 24. The cylinder may be provided with a needle 30 through which liquid is to be transported. The syringe 22 is of a conventional type with a shoulder 32 at the top end of the cylinder 24 to enable finger retention while the plunger 26 is engaged at its top end 34. The plunger, which is shown extended, has a piston in cylinder 24, not visible in the view of FIG. 1, to push liquid through needle 30 for dispensing.

The actuator 20 enables one to move the plunger 26 in small discrete steps in the direction indicated by arrow 36 to dispense identical quantities of liquid for each actuation. The amount to be dispensed depends upon the crosssectional area of syringe cylinder 24 and the discrete advance of the plunger 26. With the actuator 20, the discrete advance is precisely controlled so that each actuation causes the dispensation of the same amount of liquid within a close tolerance.

The actuator is formed with a main body 38 provided with a finger actuatable pusher 40 and a plunger engager 42. The pusher 40 is mounted for reciprocal motion on main body 38 and is located adjacent plunger engager 42 which is mounted for sliding movement to main body 38. A ratchet mechanism 44 is interposed between the plunger actuator 42 and pusher 40 to provide the precise discrete advance.

The ratchet mechanism 44 is formed of a rack 46 located along a surface 48 facing the pusher surface 50.

The rack 46 extends along the length of surface 48. The pusher surface 50 is provided with a pawl 52 located to engage the back side 54 of teeth 56 of rack 46 to enable successive advancements of the plunger actuator 42.

The reciprocal mounting of the finger actuatable pusher 40 is obtained within a slot 58 of main body 38 as more particularly illustrated and described with reference to FIGS. 3 and 5. The pusher 40 is shown in FIG. 2 trapped within a spring retaining slot 60 enclosing a compressible spring 62 shown in its normal extended position. The spring 62 is captured in a cut-out 64 of pusher 48 and engages one end 66 thereof while a pin 68, driven through main body and slot 60 holds the spring 62 in position.

The other end 70 of cut-out 64 is located near a motion limiting pin 72 is also driven through main body 38 and slot 60. The pusher 40 may thus be advanced along the direction of arrow 36 by thumb-applied pressure on a tab 74 and against the bias of spring 62. This advance may continue until the back surface 76 of pusher 40 encounters an adjustable stop element 78. The latter is in the form of a screw placed in a suitably threaded bore 80 aligned with the slot 60.

When the thumb pressure on pusher 40 is released, spring 62 reverses the pusher to enable pawl 52 to engage a different tooth 56 on rack 46. The location of the stop element 76 enables one to select one or more successive tooth spacings as the incremental motions for plunger 26. The latter is engaged by a plunger tab 82 extending upwardly from the plunger actuator for contact with the top 34 of plunger 26. A spring 82 is used with stop element 78 to provide a bias force for holding its position.

A finger tab 84 is shown mounted in a transverse slot 86 of main body 38 to enable finger retention of the actuator. The finger tab 84 has a shoulder segment 88 sized to cover the pins 68, 72 driven into main body 38.

The syringe cylinder 24 is mounted to an upper surface 90 of main body 38 with the syringe shoulder 32 extending into a slot 92. A pad 81 may be bonded to surface 90 to slightly elevate the syringe 22 when a better fit can be obtained. A clip 94 is provided to enclose the cylinder 24 and temporarily fasten it to the main body 38 with a screw 96.

The reciprocal motion of pusher 40 is needed to enable convenient finger motion for the operation of the actuator. The plunger actuator 42, however, is kept in operative contact with plunger 26 by employing a back motion inhibitor 98. The back motion inhibitor 38 permits pluner actuator motion in the direction of arrow 36 while inhibiting reversal in the opposite direction.

The back motion inhibitor 98 is formed with a fibrous material 100 wherein the fibers have an inclination towards the direction of arrow 36. A fiber engager 100 in the form of a number of rack teeth 56 are used to enter the fibrous material 100 whose inclined fibers inhibit movement of the plunger engager 42 opposite to the direction of arrow 36. The fibrous material 100 is mounted in an assembly which is affixed to the main body 38 as will be explained with reference to FIGS. 8 and 9.

A number of rack teeth are employed to inhibit back motion as the rack 48 is successively advanced by operation of actuator 20. As a result, the use of a fibrous material 100 is particularly advantageous since the inhibiting force is distributed over an area and does not rely upon precise mechanical alignments.

A particular advantage of a syringe actuator in accordance with the invention resides in the use of components whose crossectional shapes and arrangement are selected to enable the use of extruded parts. This feature may be appreciated with reference to FIGS. 3, 4, 5, 6, 9, 10 and 11.

With the end view of FIG. 3 and the perspective view of the main body 38 in FIG. 5 the main body is shown formed in a generally U shaped uniform crossection with a central slot 102. The slot 102 is shaped to form a pair of parallel recesses or slots 104, 106 separated by a pair of ridges 106, 108. The lower sliding slots 104 are on opposite sides of generally cylindrical bottom located spring retaining slot 60. A pair of clip receiving slots 110, 112 are shown to extend along the outside surface of main body 38.

The finger actuatable pusher 40 is shown in FIG. 6 to be formed of a generally T shaped uniform crossection with the leg 114 of the T being sized to slidingly fit in the spring retaining slot 60 of the central slot 102 of main body 38. The crossbar segment of the T has a recessed surface 50 on which pawl 52 is mounted and is shaped to slide along lower slot 104 in the main body.

The plunger actuator 42 as shown in FIG. 9 also has a generally T shaped uniform crossectional shape with the crossbar segment 116 sized to slide in upper slots 106 with the rack provided surface 46 facing surface 50 of the pusher 40. A segment of the leg of the plunger actuater extends upwardly out of the central slot 102 to form extension 80 to engage the plunger 26.

The finger tab 84 as illustrated in FIG. 10 and the clip 94 shown in FIG. 3 also have uniform extrudable crossection. In this manner the main components of the actuator may be extruded from a suitable material such as aluminum. The extrusion dimensions needed to obtain accurate performance with the actuator are available from precision extruders. Particularly precise dimensional control may be needed for such slots as 104 and 106 to reduce loose fit movements of the pusher 40 and plunger engager 42.

The extrusion of the main components of the actuator 20 is followed with a minimum of machining work. Thus the slots 86 and 98 are milled in a main body 38, while holes for pins 68, 72 and bore 80 are drilled and the latter threaded for the screw stop element 78. The cut-out 74 is milled into the pusher 40 while the rack teeth 56 also are machined after extrusion.

The back motion inhibitor 98 is formed as illustrated in FIGS. 8 and 9 with a segment 120 of extruded pusher material. The bottom leg segment 114' is reduced in length so as to avoid interference with the stop element 78 as shown in FIG. 2. A generally rectangular fibrous segment 100 is cut from a material such as FIBER-TRAN, a nylon brush-like material with angled fibers made by the MMM Company of St. Paul Minn. A metal support 122 is formed, sized to fit flush on the recessed surface 50 of the segment 120. An edge 124 is bent over at an angle selected to provide back motion inhibiting support for those fibers which are located near the edge of segment 100. Generally, edge 124 is inclined parallel to the inclination of the fibers.

The segment 100, the support 122 and the extruded segment 120 are bonded together as shown in FIG. 6 with a suitable adhesive. The entire back motion inhibitor 98 is then inserted at an end of main body 38 as shown in FIG. 2 and bonded in place.

An advantage with the back motion inhibitor 98 resides in that a reasonably small amount of fibrous material can be used. The edge backing by support 124 enables full area utilization to form a practical, convenient and easily assembled back motion inhibitor.

As previously described, a multiple number of pawls 52 may be used. FIG. 12 illustrates a pair 52, 52' which are sequentially so spaced that their teeth contacting stop edges 126 are separated at one-half the spacing between successive teeth 56, 56'. In this manner as one pawl seats against a tooth edge 54, the other rests midway against another tooth 56. Successive actuations will then enable alternate seating of the pawls with the result of smaller incremental advances of the plunger actuator 42. The pawls 52 can be made replaceable.

Having thus described a syringe actuator in accordance with the invention, its advantages can be appreciated. Modifications may be contemplated for the described embodiment for a dispenser. For example, the rack teeth 56 and pawl 52 and back motion inhibitor 98 can be reversed in position to obtain an incremental extraction of the plunger 26 to correspondingly take up equal small quantities of material. In such case the segment 80 used to contact the top end 34 of the plunger 26 can be appropriately modified to engage and move the plunger.

Another modification would utilize the same type of fibrous material 100 used on the back motion inhibitor 98 either with or without a metal support similar to 124 in FIG. 8 to replace the pawl 52 in FIG. 6. In this embodiment the fibrous material would be cut to a size approx. equal to the recess in item 50 of FIG. 6 and affixed to its surface so that the fibers angle is in the same direction as the pawl 52 it replaces. This arrangement due to the large number and randomness of the fibers provides a system analogous to a multiple pawl with thousands of elements. When this configuration is used in conjunction with the stop element 78 a stroke control that is essentialy stepless and infinitely adjustable is contained.

What is claimed is:

1. A manually actuated mechanism for causing relative motion between a plunger and a cylinder of a syringe with precise incremental steps to enable the transport of precise quantities of liquid through the open end of the syringe comprising
   a main body having a surface shaped to support the syringe with the plunger located alongside said surface for said relative movement in a liquid transport direction;
   a plunger actuator slidingly mounted to the main body for movement along the liquid transport direction, said plunger actuator being shaped to engage a plunger of a syringe mounted on the main body surface and move the plunger along said liquid transport direction;
   a finger actuatable pusher movingly mounted adjacent the plunger actuator on the main body for reciprocating motion along said liquid transport direction;
   a ratchet mechanism operatively mounted to the plunger actuator and the pusher to provide incremental advance of the plunger actuator upon reciprocal movement of the pusher; and
   a back motion inhibitor operatively mounted between the plunger actuator and the main body, said inhibitor being oriented to enable movement of the plunger in said liquid transport direction while preventing reverse movement of the plunger actuator.

2. The mechanism for causing liquid transport through the open end of a syringe as claimed in claim 1 wherein the main body is further provided with an adjustable stop element located to limit movement of the pusher to an amount selected as a predetermined multiple of the smallest incremental advance provided by the ratchet mechanism.

3. The mechanism for causing liquid transport through the open end of a syringe as claimed in claim 1 wherein the back motion inhibitor is formed of a fibrous material and a fiber material engager having an effectively angled entry with the fibrous material selected to enable movement of the plunger actuator in the liquid transport direction while resisting reverse movement thereof.

4. The mechanism for causing liquid transport through the open end of a syringe as claimed in claim 3 wherein the ratchet mechanism is formed of a rack and pawl, the rack having a plurality of spaced teeth extending over a distance commensurate with the full motion of a syringe plunger, said rach further extending opposite the fibrous material to provide teeth as a plurality of fiber material engagers over the length of the fibrous material exposed to said teeth.

5. The mechanism for causing liquid transport through the open end of a syringe as claimed in claim 4 wherein the fibrous material is formed of a material with fibers which are inclined at an angle relative to a direction normal to the surface of the fibrous material.

6. The mechanism for causing liquid transport through the open end of a syringe as claimed in claim 5 wherein the back motion inhibitor is in the form of an assembly composed of a support shaped to fit in back of the fibrous material and provided with an edge which bends around an edge of the fibrous material generally in parallel with the inclined fibers to provide back motion inhibiting support for fibers located near said edge of the fibrous material.

7. The mechanism for causing liquid transport through the open end of a syringe as claimed in claim 4 wherein the ratchet mechanism is provided with a plurality of pawls which are effectively spaced to obtain sequential operative contact with the rack teeth to produce incremental advances which are less than the spacing between successive rack teeth.

8. The mechanism for causing liquid transport through the open end of a syringe as claimed in claim 1 wherein the main body is formed of an extruded metal body provided with a central slot shaped to slidingly retain both the plunger actuator and the pusher adjacent to each other.

9. The mechanism for causing liquid transport through the open end of a syringe as claimed in claim 8 wherein the extruded metal body central slot is further shaped to form a spring retaining slot, said finger actuatable pusher being formed of generally T shaped crossectional extruded metal, with the leg of the T shaped pusher sized to extend into the spring retaining slot of the extruded metal body.

10. The mechanism for causing liquid transport through the open end of a syringe as claimed in claim 9 wherein the plunger actuator is formed of a generally T crossectional shaped extruded metal piece sized to fit within the central slot of the main body, with the crossbar segment of the T shaped plunger actuator facing the crossbar segment of the T shaped pusher, with a selected pusher segment of the leg of the T shaped plunger actuator extending out of the central slot of the main body to contact the plunger of a syringe mounted to the main body.

11. The mechanism for causing liquid transport through the open end of a syringe as claimed in claim 10 wherein the crossbar segment of the plunger actuator is provided with a toothed rack, with its teeth oriented to enable the plunger actuator segment which engages the plunger of a syringe to move the plunger in the liquid transport direction and wherein the crossbar segment of the T shaped pusher is provided with a pawl sized and shaped to operatively engage the teeth of the rack.

12. The mechanism for causing liquid transport through the open end of a syringe as claimed in claim 11 wherein the leg of the T shaped pusher is further provided with a spring capturing slot, a spring in the spring retaining slot of the main body, and a trapping pin extending through the main body and the spring retaining slot to trap the spring.

13. The mechanism for causing liquid transport through the open end of a syringe as claimed in claim 12 wherein the main body is further provided with a threaded borehole in axial alignment with the spring retaining slot of the central slot, and an adjustable stop screw sized to thread in the bore hole to contact the pusher for control of its reciprocating stroke.

* * * * *

UNITED STATES PATENT OFFICE
CERTIFICATE OF CORRECTION

Patent No. 4,022,207   Dated May 10, 1977

Inventor(s) Paul S. Citrin

It is certified that error appears in the above-identified patent and that said Letters Patent are hereby corrected as shown below:

Col. 3, line 40, "81" should be replaced by --91--.

Col. 5, line 38, "contained" should be replaced by --obtained--.

Col. 6, line 21, "rach" should be replaced by --rack--.

Signed and Sealed this

Thirteenth Day of September 1977

[SEAL]

Attest:

RUTH C. MASON
Attesting Officer

LUTRELLE F. PARKER
Acting Commissioner of Patents and Trademarks